US00PP08020P

United States Patent [19]

Benardella

[11] Patent Number: Plant 8,020

[45] Date of Patent: Nov. 3, 1992

[54] HYBRID MINIATURE ROSE PLANT NAMED BENFIG

[75] Inventor: Frank A. Benardella, Old Tappan, N.J.

[73] Assignee: Weeks Wholesale Rose Grower, Inc., Upland, Calif.

[21] Appl. No.: 664,219

[22] Filed: Feb. 28, 1991

[51] Int. Cl.[5] ..... A01H 5/00
[52] U.S. Cl. ..... Plt./7.1
[58] Field of Search ..... Plt./7, 8, 9, 22, 26

[56] References Cited

U.S. PATENT DOCUMENTS

P.P. 4,636 2/1981 Strawn ..... Plt. 7

*Primary Examiner*—Howard J. Locker
*Attorney, Agent, or Firm*—Chrisite, Parker & Hale

[57] ABSTRACT

A new variety of hybrid miniature rose plant producing large long urn-shaped buds, flowers with delicate colorations of white edged with pink and long stems.

1 Drawing Sheet

BACKGROUND OF THE INVENTION

This invention relates to a new and distinct variety of hybrid miniature rose. The plant is of a dwarf, bushy growth habit suitable for growing outdoor for garden decoration and also for producing cut flowers. It has as its seed parent the variety known as 'Rise 'n' Shine' (U.S. Plant Pat. No. 4,231) and as its pollen parent the variety known as 'Laguna' (unpatented). The varietal denomination of the new variety is 'Benfig'.

SUMMARY OF THE INVENTION

Among the features which distinguish the new variety from other cultivars are the following combination of characteristics: large long urn-shaped buds, delicate colorations of white edged with pink substantially as described and illustrated herein, long stems suitable for cut flower production, and its vigorous free-flowering plant. 'Benfig' may be propagated by cuttings, budding, grafting and tissue culture.

Asexual propagation of the new variety by cuttings and budding as performed in Kern County and Upland, Calif., has shown that the foregoing and other distinguishing characteristics come true to form and are established and transmitted through succeeding propagations.

COMPARISON WITH PARENT VARIETIES

The new rose may be distinguished from its seed parent, 'Rise 'n' Shine' by the following combination of characteristics: whereas the seed parent produces flowers of a uniform yellow coloration, 'Benfig' produces white flowers with a pink picotee essentially as described and illustrated herein. Whereas the new cultivar bears large long pointed buds, large flowers and foliage for the class, 'Rise 'n' Shine' bears significantly smaller buds, flowers and foliage. 'Benfig' produces stems which are long for the class and which are suitable for cut flower production, whereas the seed parent bears significantly shorter stems not suited for cut flower production.

The new variety may be distinguished form its pollen parent, 'Laguna' by the following combination of characteristics: whereas the pollen parent is a Floribunda, 'Benfig' is a Miniature, being significantly smaller in flower, foliage and stem. 'Laguna' produces flowers of a relatively uniform lavender coloration, whereas 'Benfig' bears white flowers with a pink picotee, essentially as aforesaid. The pollen parent has a very strong fragrance, whereas the new cultivar has significantly lighter fragrance.

BRIEF DESCRIPTION OF THE ILLUSTRATION

The accompanying photograph illustrates the plant in color and shows the flowering thereof from bud to full bloom depicted in color as nearly correct as it is possible to make in an illustration of this character. Throughout this specification, color names and values are based upon the Colour Chart of The Royal Horticultural Society of London, England, except where common terms of color definition are employed.

DESCRIPTION OF NEW VARIETY

The following description pertains to rose plants of the new cultivar grown outdoors in October, in Upland, Calif. and is believed to apply to plants of the variety grown elsewhere in similar conditions of soil and climate.

FLOWER

The new variety bears its flowers sometimes singly, usually three to four or more per stem. Flowers are borne in irregular flat to rounded clusters on strong long stems for this class. Outdoor the plant blooms very freely and nearly continuously during the growing season. The flowers have a slight tea fragrance.

BUD

The peduncle is of short to average length for the class, of average to heavy caliper, and usually erect and stiff. It is almost entirely smooth with some hairs and few stipitate glands. Peduncle color is between Yellow-Green 144A and Green 137A. Before the calyx breaks, the bud is moderately large for the class, moderately long in length, and very pointed in shape. The surface of the bud is almost entirely smooth with few stipitate glands and fine hairs, usually with slender entire foliaceous parts extending beyond the tip of the bud equal to ¾ or more of its length. Bud color is between Yellow-Green 144A and Green 137A.

The inner surface of the sepals is lined with fine woolly tomentum; sepal margins are lined with few stipitate glands and hairs.

As the first petals open, the bud is moderately large for the class, of moderately long length, and very pointed to urn-shaped in form. The color of the outside surfaces of the newly opened petals is between Yellow-White 158D and White 155D. The very edge of the petal is finely edged with between Red 56A and Red 56B. The color of the inside surfaces of the newly opened petals is as above with a broader wash at the very edge of the petal of between Red 56A and Red 56B. It opens well in wet, cold, hot or dry weather.

BLOOM

When fully open, the bloom is moderately large for the class, ranging from 6 to 7 cms. in diameter. Petalage is double with 26 to 30 petals and 2 to 5 petaloids arranged regularly. When partially open, the bloom form is very high centered and the petals are moderately reflexed outward. When fully open, the bloom form is somewhat flat to cupped and the petals are more undulated with petal edges more reflexed to quilled outward.

PETALS

The petals are of moderately heavy substance and of medium thickness, with inside surfaces slightly satiny to velvety and outside surfaces slightly shiny to satiny. The outside petals are nearly round to broadly obovate in shape with apices somewhat mucronate. The inside petals are more narrowly obovate to lanceolate in shape with slightly mucronate apices.

The color values and the following description are of flowers a plant grown outdoor in Upland, Calif. in the month of October. Colors may be modified by being washed or shaded or tinted with other colors.

NEWLY OPENED FLOWER

The outside surface of the outer, intermediate and inner petals is between White 155B and White 155D with a very small zone at the very base point of petal attachment, of near Yellow 2C. The very edge of the outside surface of the petal is washed with between Red 56A and Red 56B. The inside surface of the outer, intermediate and inner petals is as above with a much broader wash at the edge of the petals of between Red 56A and Red 56B.

The general tonality of the newly opened flower is between White 155B and White 155D edged with a wash of between Red 56A and Red 56B.

THREE DAY OLD FLOWER

The outside surface of the outer and inner petals is between White 155D and White 155A. The very edge of the outside surface of the petal is washed with between Red 56C and Red 56D. The inside surface of the outer and inner petals is as above with a somewhat broader wash at the edge of the petals of between Red 56C and Red 56D.

The general tonality of a three day old flower is between White 155D and White 155A, slightly blushed with a wash of between Red 56C and Red 56D.

On the spent bloom, the petals usually drop off cleanly fading to near White 155D, and are not particularly affected by changes in weather.

In October, blooms on the bush growing in the garden generally last from three to four or more days. Cut flowers, from plants grown outdoor, kept at normal indoor living temperatures generally last from three to four or more days. Cut flowers, from plants grown in a greenhouse, kept at normal indoor living temperatures generally last from four to five or more days.

MALE REPRODUCTIVE ORGANS

Stamens are average in number and are arranged regularly about the pistil. The filaments are moderately long, most with anthers. The anthers are somewhat large for the class and all open approximately at the same time. Anther color is near Yellow-Orange 15A when immature and near Greyed-Orange 177A at maturity. Pollen is moderate and near Yellow-Orange 16C in color.

FEMALE REPRODUCTIVE ORGANS

Pistils are somewhat few in number (approximately 25). The styles are moderately even, short to average in length, somewhat thin in caliper, and somewhat loosely bunched. Stigma color is near Red 43D. Ovaries are usually all enclosed in the calyx.

Hips have not been observed on this variety in Upland, Calif.

FOLIAGE

The compound leaves are usually comprised of three to five, sometimes seven leaflets and are borne in moderately abundant quantities. The leaves are moderately large for the class, somewhat heavy to leathery in texture, and somewhat semi-glossy to matte in finish. The leaflets are shaped moderately ovate with somewhat acute to acuminate apices and moderately round to acute bases. Their margins are somewhat doubly serrate to irregular.

The upper surface of the mature leaf is between Yellow-Green 147A and Green 136A. The undersurface of the mature leaf is between Yellow-Green 148B and Green 138B. The upper surface of the young leaf is between Yellow-Green 147A and Green 136A, sometimes lightly suffused with between Greyed-Orange 176A and Greyed-Purple 183C. The undersurface of the young leaf is between Yellow-Green 148B and Green 137B, often heavily suffused with between Greyed-Orange 176A and Greyed-Purple 183C.

The rachis is moderately heavy in caliper, very smooth and grooved with few stipitate glands on the edges of the upper side. The underside of the rachis is moderately smooth with few prickles.

The stipules are of short to medium length with moderately narrow width and short to medium straight points that usually turn out at an angle of about 45 degrees.

The plant displays an average degree of resistance to powdery mildew and rust as compared to other commercial varieties grown under comparable conditions in Upland, Calif.

GROWTH

The plant is dwarf bushy medium height habit, 18 to 20 inches at maturity, with moderately full branching. It displays very vigorous growth and the canes are of medium to heavy caliper for the class.

The major stems are between Yellow-Green 146A and Green 137C. They bear few large prickles which are medium length to long for the class. The large prickles are almost straight but hooked slightly downward, with a medium length, moderately narrow base; prickle color is near Greyed-Orange 165A. The major stem bears no small prickles and no hairs.

The branches are between Yellow-Green 147A and Green 137A. They bear a few large prickles which are of medium length to long for the class. The large prickles are almost straight but hooked slightly downward, with a medium length, moderately narrow base; prickle color is between Greyed-Orange 165B and Greyed-Orange 166C. The branches bear few small prickles of similar coloration and no hairs.

The new shoots are near Yellow-Green 147A often heavily suffused with between Greyed-Orange 176C and Greyed-Purple 183C. They bear a few large prickles which are medium length to long for the class. The large prickles are almost straight but hooked slightly downward with a medium length, moderately narrow base; prickle color is between Greyed-Orange 176C and Greyed-Red 178A. The shoots bear few small prickles of similar coloration and no hairs.

I claim:

1. A new and distinct variety of the miniature rose class, substantially as shown and described.

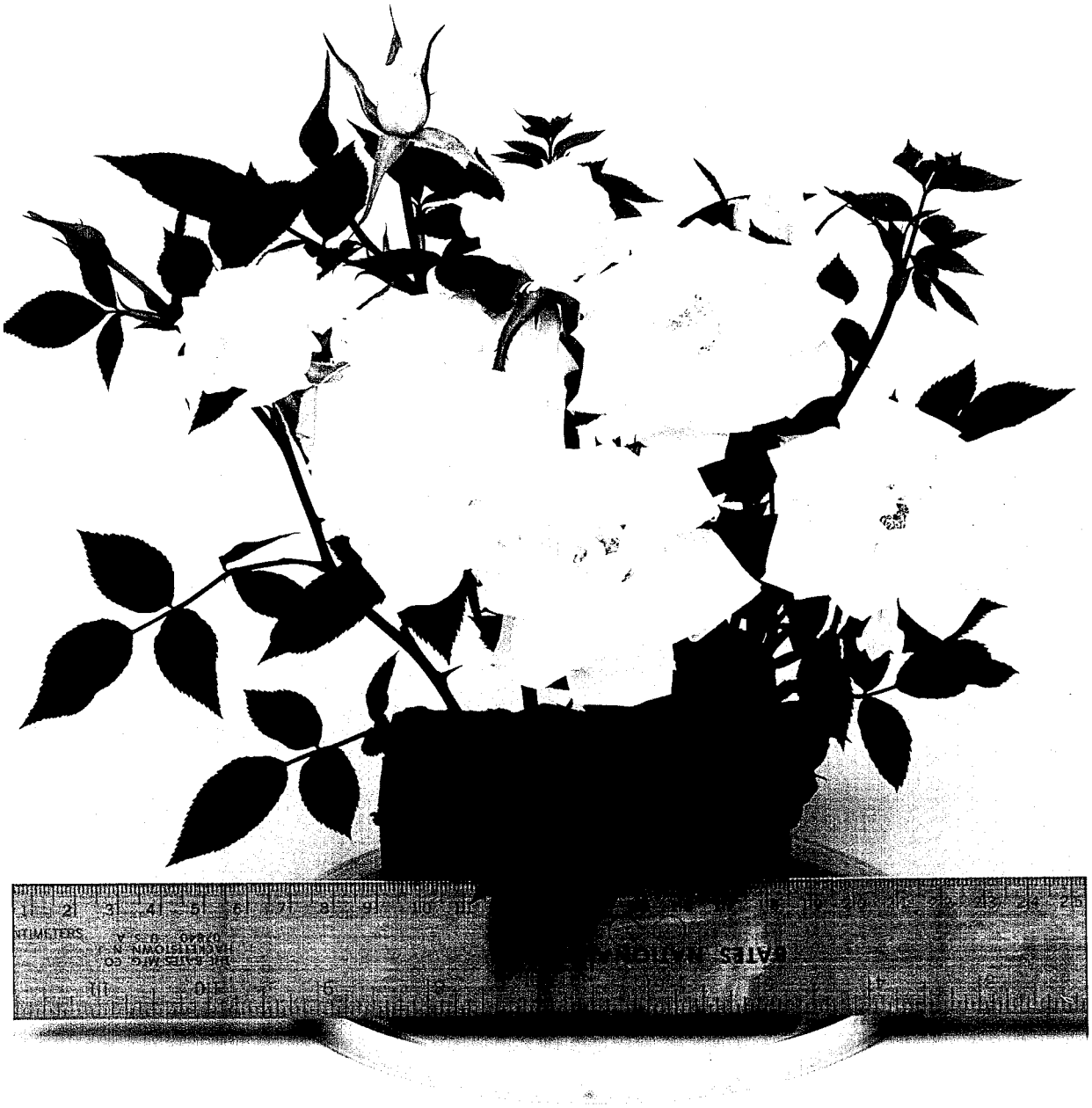

* * * * *